United States Patent [19]

Soon-Shiong et al.

[11] Patent Number: 5,560,933
[45] Date of Patent: Oct. 1, 1996

[54] METHODS FOR IN VIVO DELIVERY OF SUBSTANTIALLY WATER INSOLUBLE PHARMACOLOGICALLY ACTIVE AGENTS AND COMPOSITIONS USEFUL THEREFOR

[75] Inventors: Patrick Soon-Shiong; Neil P. Desai, both of Los Angeles; Mark W. Grinstaff, Pasadena; Paul A. Sandford, Los Angeles, all of Calif.; Kenneth S. Suslick, Champaign, Ill.

[73] Assignee: VivoRx Pharmaceuticals, Inc., Santa Monica, Calif.

[21] Appl. No.: 412,726

[22] Filed: Mar. 29, 1995

Related U.S. Application Data

[62] Division of Ser. No. 23,698, Feb. 22, 1993, Pat. No. 5,439,686.

[51] Int. Cl.⁶ ......................................................... A61K 9/14
[52] U.S. Cl. ........................... 424/489; 424/451; 424/465; 424/9.1; 424/9.341
[58] Field of Search ..................................... 424/465, 489, 424/451; 128/660; 427/2.12

[56] References Cited

U.S. PATENT DOCUMENTS

| | | | |
|---|---|---|---|
| 4,718,433 | 1/1988 | Feinstein | 128/660 |
| 5,344,640 | 9/1994 | Deutsch et al. | 424/9 |
| 5,370,901 | 12/1994 | Tournier et al. | 427/2.12 |
| 5,439,686 | 8/1995 | Desai et al. | 424/451 |

Primary Examiner—Thurman K. Page
Assistant Examiner—William E. Benston, Jr.
Attorney, Agent, or Firm—Pretty, Schroeder, Brueggemann & Clark; Stephen E. Reiter

[57] ABSTRACT

In accordance with the present invention, there are provided compositions for the in vivo delivery of substantially water insoluble pharmacologically active agents (such as the anti-cancer drug taxol) in which the pharmacologically active agent is delivered in a soluble form or in the form of suspended particles. In particular, the soluble form may comprise a solution of pharmacologically active agent in a biocompatible dispersing agent contained within a protein walled shell. Alternatively, the protein walled shell may contain particles of taxol. In another aspect, the suspended form comprises particles of pharmacologically active agent in a biocompatible aqueous liquid.

28 Claims, No Drawings

METHODS FOR IN VIVO DELIVERY OF SUBSTANTIALLY WATER INSOLUBLE PHARMACOLOGICALLY ACTIVE AGENTS AND COMPOSITIONS USEFUL THEREFOR

This application is a divisional of application Ser. No. 08/023,698, filed Feb. 22, 1993. now U.S. Pat. No. 5,439,686.

The present invention relates to in vivo delivery of substantially water insoluble pharmacologically active agents (e.g., the anticancer drug taxol). In one aspect, the agent is dispersed as a suspension suitable for administration to a subject, or is dissolved in a suitable biocompatible liquid. In another aspect, water insoluble pharmacologically active agents (e.g., taxol) are encased in a polymeric shell formulated from a biocompatible polymer. The polymeric shell contains particles of pharmacologically active agent, and optionally a biocompatible dispersing agent in which pharmacologically active agent can be either dissolved or suspended.

BACKGROUND OF THE INVENTION

Taxol is a natural product first isolated from the Pacific Yew tree, *Taxus brevifolia*, by Wani et al. [J. Am. Chem. Soc. Vol. 93:2325 (1971)]. Among the antimitotic agents, taxol, which contains a diterpene carbon skeleton, exhibits a unique mode of action on microtubule proteins responsible for the formation of the mitotic spindle. In contrast with other antimitotic agents such as vinblastine or colchicine, which prevent the assembly of tubulin, taxol is the only plant product known to inhibit the depolymerization process of tubulin, thus preventing the cell replication process.

Taxol, a naturally occurring diterpenoid, has been shown to have significant antineoplastic and anticancer effects in drug-refractory ovarian cancer. Taxol has shown excellent antitumor activity in a wide variety of tumor models such as the B16 melanoma, L1210 leukemias, MX-1 mammary tumors, and CS-1 colon tumor xenografts. Several recent press releases have termed taxol as the new anticancer wonder-drug. Indeed, taxol has recently been approved by the Federal Drug Administration for treatment of ovarian cancer. The poor aqueous solubility of taxol, however, presents a problem for human administration. Indeed, the delivery of drugs that are inherently insoluble or poorly soluble in an aqueous medium can be seriously impaired if oral delivery is not effective. Accordingly, currently used taxol formulations require a cremaphore to solubilize the drug. The human clinical dose range is 200–500 mg. This dose is dissolved in a 1:1 solution of ethanol:cremaphore and diluted to one liter of fluid given intravenously. The cremaphore currently used is polyethoxylated castor oil.

In phase I clinical trials, taxol itself did not show excessive toxic effects, but severe allergic reactions were caused by the emulsifiers employed to solubilize the drug. The current regimen of administration involves treatment of the patient with antihistamines and steroids prior to injection of the drug to reduce the allergic side effects of the cremaphore.

In an effort to improve the water solubility of taxol, several investigators have modified its chemical structure with functional groups that impart enhanced water-solubility. Among them are the sulfonated derivatives [Kingston et al., U.S. Pat. No. 5,059,699 (1991)], and amino acid esters [Mathew et al., J. Med. Chem. Vol. 35:145–151 (1992)] which show significant biological activity. Modifications to produce a water-soluble derivative facilitate the intravenous delivery of taxol dissolved in an innocuous carrier such as normal saline. Such modifications, however, add to the cost of drug preparation, may induce undesired side-reactions and/or allergic reactions, and/or may decrease the efficiency of the drug.

Microparticles and foreign bodies present in the blood are generally cleared from the circulation by the 'blood filtering organs', namely the spleen, lungs and liver. The particulate matter contained in normal whole blood comprises red blood cells (typically 8 microns in diameter), white blood cells (typically 6–8 microns in diameter), and platelets (typically 1–3 microns in diameter). The microcirculation in most organs and tissues allows the free passage of these blood cells. When microthrombii (blood clots) of size greater than 10–15 microns are present in circulation, a risk of infarction or blockage of the capillaries results, leading to ischemia or oxygen deprivation and possible tissue death. Injection into the circulation of particles greater than 10–15 microns in diameter, therefore, must be avoided. A suspension of particles less than 7–8 microns, is however, relatively safe and has been used for the delivery of pharmacologically active agents in the form of liposomes and emulsions, nutritional agents, and contrast media for imaging applications.

The size of particles and their mode of delivery determines their biological behavior. Strand et al. [in *Microspheres-Biomedical Applications*, ed. A. Rembaum, pp 193–227, CRC Press (1988)] have described the fate of particles to be dependent on their size. Particles in the size range of a few nanometers (nm) to 100 nm enter the lymphatic capillaries following interstitial injection, and phagocytosis may occur within the lymph nodes. After intravenous/intraarterial injection, particles less than about 2 microns will be rapidly cleared from the blood stream by the reticuloendothelial system (RES), also known as the mononuclear phagocyte system (MPS). Particles larger than about 7 microns will, after intravenous injection, be trapped in the lung capillaries. After intraarterial injection, particles are trapped in the first capillary bed reached. Inhaled particles are trapped by the alveolar macrophages.

Pharmaceuticals that are water-insoluble or poorly water-soluble and sensitive to acid environments in the stomach cannot be conventionally administered (e.g., by intravenous injection or oral administration). The parenteral administration of such pharmaceuticals has been achieved by emulsification of the oil solubilized drug with an aqueous liquid (such as normal saline) in the presence of surfactants or emulsion stabilizers to produce stable microemulsions. These emulsions may be injected intravenously, provided the components of the emulsion are pharmacologically inert. U.S. Pat. No. 4,073,943 describes the administration of water-insoluble pharmacologically active agents dissolved in oils and emulsified with water in the presence of surfactants such as egg phosphatides, pluronics (copolymers of polypropylene glycol and polyethylene glycol), polyglycerol oleate, etc. PCT International Publication No. W085/00011 describes pharmaceutical microdroplets of an anaesthetic coated with a phospholipid such as dimyristoyl phosphatidylcholine having suitable dimensions for intradermal or intravenous injection.

Protein microspheres have been reported in the literature as carriers of pharmacological or diagnostic agents. Microspheres of albumin have been prepared by either heat denaturation or chemical crosslinking. Heat denatured microspheres are produced from an emulsified mixture (e.g., albumin, the agent to be incorporated, and a suitable oil) at temperatures between 100° C. and 150° C. The microspheres are then washed with a suitable solvent and stored.

Leucuta et al. [International Journal of Pharmaceutics Vol. 41:213–217 (1988)] describe the method of preparation of heat denatured microspheres.

The procedure for preparing chemically crosslinked microspheres involves treating the emulsion with glutaraldehyde to crosslink the protein, followed by washing and storage. Lee et al. [Science Vol. 213:233–235 (1981)] and U.S. Pat. No. 4,671,954 teach this method of preparation.

The above techniques for the preparation of protein microspheres as carriers of pharmacologically active agents, although suitable for the delivery of water-soluble agents, are incapable of entrapping water-insoluble ones. This limitation is inherent in the technique of preparation which relies on crosslinking or heat denaturation of the protein component in the aqueous phase of a water-in-oil emulsion. Any aqueous-soluble agent dissolved in the protein-containing aqueous phase may be entrapped within the resultant crosslinked or heat-denatured protein matrix, but a poorly aqueous-soluble or oil-soluble agent cannot be incorporated into a protein matrix formed by these techniques.

BRIEF DESCRIPTION OF THE INVENTION

Thus it is an object of this invention to deliver pharmacologically active agents (e.g., taxol, taxane, Taxotere, and the like) in unmodified form in a composition that does not cause allergic reactions due to the presence of added emulsifiers and solubilizing agents, as are currently employed in drug delivery.

It is a further object of the present invention to deliver pharmacologically active agents in a composition of microparticles suspended in a suitable biocompatible liquid.

It is yet another object of the invention to deliver pharmacologically active agents enclosed within a polymer shell which is further suspended in a biocompatible liquid.

These and other objects of the invention will become apparent upon review of the specification and claims.

In accordance with the present invention, we have discovered that substantially water insoluble pharmacologically active agents can be delivered in the form of microparticles that are suitable for parenteral administration in aqueous suspension. This mode of delivery obviates the necessity for administration of substantially water insoluble pharmacologically active agents (e.g., taxol) in an emulsion containing, for example, ethanol and polyethoxylated castor oil, diluted in normal saline (see, for example, Norton et al., in Abstracts of the 2nd National Cancer Institute Workshop on Taxol & Taxus, Sep. 23–24, 1992). A disadvantage of such known compositions is their propensity to produce allergic side effects.

The delivery of substantially water insoluble pharmacologically active agents in the form of a microparticulate suspension allows some degree of targeting to organs such as the liver, lungs, spleen, lymphatic circulation, and the like, through the use of particles of varying size, and through administration by different routes. The invention method of delivery further allows the administration of substantially water insoluble pharmacologically active agents employing a much smaller volume of liquid and requiring greatly reduced administration time relative to administration volumes and times required by prior art delivery systems (e.g., intravenous infusion of approximately one to two liters of fluid over a 24 hour period are required to deliver a typical human dose of 200–400 mg of taxol).

In accordance with another embodiment of the present invention, we have developed compositions useful for in vivo delivery of substantially water insoluble pharmacologically active agents. Invention compositions comprise substantially water insoluble pharmacologically active agents (as a solid or liquid) contained within a polymeric shell. The polymeric shell is a biocompatible polymer, crosslinked by the presence of disulfide bonds. The polymeric shell, containing substantially water insoluble pharmacologically active agents therein, is then suspended in a biocompatible aqueous liquid for administration.

DETAILED DESCRIPTION OF THE INVENTION

In accordance with the present invention, there are provided compositions for in vivo delivery of a substantially water insoluble pharmacologically active agent, wherein said agent is a solid or liquid substantially completely contained within a polymeric shell, wherein the largest cross-sectional dimension of said shell is no greater than about 10 microns, wherein said polymeric shell comprises a biocompatible polymer which is substantially crosslinked by way of disulfide bonds, and wherein said polymeric shell containing pharmacologically active agent therein is suspended in a biocompatible aqueous liquid.

As used herein, the term "in vivo delivery" refers to delivery of a pharmacologically active agent by such routes of administration as oral, intravenous, subcutaneous, intraperitoneal, intrathecal, intramuscular, inhalational, topical, transdermal, suppository (rectal), pessary (vaginal), and the like.

As used herein, the term "micron" refers to a unit of measure of one one-thousandth of a millimeter.

As used herein, the term "biocompatible" describes a substance that does not appreciably alter or affect in any adverse way, the biological system into which it is introduced.

Key differences between the pharmacologically active agents contained in a polymeric shell according to the invention and protein microspheres of the prior art are in the nature of formation and the final state of the protein after formation of the particle, and its ability to carry poorly aqueous-soluble or substantially aqueous-insoluble agents. In accordance with the present invention, the polymer (e.g., a protein) is selectively chemically crosslinked through the formation of disulfide bonds through, for example, the amino acid cysteine that occurs in the natural structure of a number of proteins. A sonication process is used to disperse a dispersing agent containing dissolved or suspended pharmacologically active agent into an aqueous solution of a biocompatible polymer bearing sulfhydryl or disulfide groups (e.g., albumin) whereby a shell of crosslinked polymer is formed around fine droplets of non-aqueous medium. The sonication process produces cavitation in the liquid that causes tremendous local heating and results in the formation of superoxide ions that crosslink the polymer by oxidizing the sulfhydryl residues (and/or disrupting existing disulfide bonds) to form new, crosslinking disulfide bonds.

In contrast to the invention process, the prior art method of glutaraldehyde crosslinking is nonspecific and essentially reactive with any nucleophilic group present in the protein structure (e.g., amines and hydroxyls). Heat denaturation as taught by the prior art significantly and irreversibly alters protein structure. In contrast, disulfide formation contemplated by the present invention does not substantially denature the protein. In addition, particles of substantially water insoluble pharmacologically active agents contained within a shell differ from crosslinked or heat denatured protein microspheres of the prior art because the polymeric shell produced by the invention process is relatively thin compared to the diameter of the coated particle. It has been determined (by transmission electron microscopy) that the "shell thickness" of the polymeric coat is approximately 25 nanometers for a coated particle having a diameter of 1 micron (1000 nanometers). In contrast, microspheres of the prior art do not have protein shells, but rather, have protein dispersed throughout the volume of the microsphere.

The polymeric shell containing solid or liquid cores of pharmacologically active agent allows for the delivery of high doses of the pharmacologically active agent in relatively small volumes. This minimizes patient discomfort at receiving large volumes of fluid and minimizes hospital stay. In addition, the walls of the polymeric shell are generally completely degradable in vivo by proteolytic enzymes (e.g., when the polymer is a protein), resulting in no side effects from the delivery system as is the case with current formulations.

According to this embodiment of the present invention, particles of substantially water insoluble pharmacologically active agents are contained within a shell having a cross-sectional diameter of no greater than about 10 microns. A cross-sectional diameter of less than 5 microns is more preferred, while a cross-sectional diameter of less than 1 micron is presently the most preferred for the intravenous route of administration.

Substantially water insoluble pharmacologically active agents contemplated for use in the practice of the present invention include pharmaceutically active agents, diagnostic agents, agents of nutritional value, and the like. Examples of pharmaceutically active agents include taxol (as used herein, the term "taxol" is intended to include taxol analogs and prodrugs, taxanes, and other taxol-like drugs, e.g., Taxotere, and the like), camptothecin and derivatives thereof (which compounds have great promise for the treatment of colon cancer), aspirin, ibuprofen, piroxicam, cimetidine, substantially water insoluble steroids (e.g., estrogen, prednisolone, cortisone, hydrocortisone, diflorasone, and the like), drugs such as phenesterine, duanorubicin, doxorubicin, mitotane, visadine, halonitrosoureas, anthrocylines, ellipticine, diazepam, and the like, anaesthetics such as methoxyfluorane, isofluorane, enfluorane, halothane, benzocaine, dantrolene, barbiturates, and the like. In addition, also contemplated are substantially water insoluble immunosuppressive agents, such as, for example, cyclosporines, azathioprine, (17-allyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3, 10,16-tetraone), prednisone, and the like. A presently preferred pharmaceutically active agent for use in the practice of the present invention is taxol, which is commercially available from the manufacturer as needle-like crystals.

Examples of diagnostic agents contemplated for use in the practice of the present invention include ultrasound contrast agents, radiocontrast agents (e.g., iodo-octanes, halocarbons, renografin, and the like), magnetic contrast agents (e.g., fluorocarbons, lipid soluble paramagnetic compounds, and the like), as well as other diagnostic agents which cannot readily be delivered without some physical and/or chemical modification to accomodate the substantially water insoluble nature thereof.

Examples of agents of nutritional value contemplated for use in the practice of the present invention include amino acids, sugars, proteins, carbohydrates, fat-soluble vitamins (e.g., vitamins A, D, E, K, and the like) or fat, or combinations of any two or more thereof.

A number of biocompatible polymers may be employed in the practice of the present invention for the formation of the polymeric shell which surrounds the substantially water insoluble pharmacologically active agents. Essentially any polymer, natural or synthetic, bearing sulfhydryl groups or disulfide bonds within its structure may be utilized for the preparation of a disulfide crosslinked shell about particles of substantially water insoluble pharmacologically active agents. The sulfhydryl groups or disulfide linkages may be preexisting within the polymer structure or they may be introduced by a suitable chemical modification. For example, natural polymers such as proteins, oligopeptides, polynucleic acids, polysaccharides (e.g., starch, cellulose, dextrans, alginates, chitosan, pectin, hyaluronic acid, and the like), and so on, are candidates for such modification.

As examples of suitable biocompatible polymers, naturally occurring or synthetic proteins may be employed, so long as such proteins have sufficient cysteine residues within their amino acid sequences so that crosslinking (through disulfide bond formation, for example, as a result of oxidation during sonication) can occur. Examples of suitable proteins include albumin (which contains 35 cysteine residues), insulin (which contains 6 cysteines), hemoglobin (which contains 6 cysteine residues per $\alpha_2\beta_2$ unit), lysozyme (which contains 8 cysteine residues), immunoglobulins, $\alpha$-2-macroglobulin, fibronectin, vitronectin, fibrinogen, and the like.

A presently preferred protein for use in the formation of a polymeric shell is albumin. Optionally, proteins such as $\alpha$-2-macroglobulin, a known opsonin, could be used to enhance uptake of the shell encased particles of substantially water insoluble pharmacologically active agents by macrophage-like cells, or to enhance the uptake of the shell encased particles into the liver and spleen.

Similarly, synthetic polypeptides containing cysteine residues are also good candidates for formation of a shell about the substantially water insoluble pharmacologically active agents. In addition, polyvinyl alcohol, polyhydroxyethyl methacrylate, polyacrylic acid, polyethyloxazoline, polyacrylamide, polyvinyl pyrrolidinone, and the like, are good candidates for chemical modification (to introduce sulfhydryl and/or disulfide linkages) and shell formation (by causing the crosslinking thereof).

In the preparation of invention compositions, one can optionally employ a dispersing agent to suspend or dissolve the substantially water insoluble pharmacologically active agent. Dispersing agents contemplated for use in the practice of the present invention include any nonaqueous liquid that is capable of suspending or dissolving the pharmacologically active agent, but does not chemically react with either the polymer employed to produce the shell, or the pharmacologically active agent itself. Examples include vegetable oils (e.g., soybean oil, coconut oil, olive oil, safflower oil, cotton seed oil, and the like), aliphatic, cycloaliphatic, or aromatic hydrocarbons having 4–30 carbon atoms (e.g., n-dodecane, n-decane, n-hexane, cyclohexane, toluene, benzene, and the like), aliphatic or aromatic alcohols having 2–30 carbon atoms (e.g., octanol, and the like), aliphatic or aromatic esters having 2–30 carbon atoms (e.g., ethyl caprylate (octanoate), and the like), alkyl, aryl, or cyclic ethers having 2–30 carbon atoms (e.g., diethyl ether, tetrahydrofuran, and the like), alkyl or aryl halides having 1–30 carbon atoms (and optionally more than one halogen substituent, e.g., $CH_3Cl$, $CH_2Cl_2$, $CH_2Cl—CH_2Cl$, and the like), ketones having 3–30 carbon atoms (e.g., acetone, methyl ethyl ketone, and the like), polyalkylene glycols (e.g., polyethylene glycol, and the like), or combinations of any two or more thereof.

Especially preferred combinations of dispersing agents include volatile liquids such as dichloromethane, ethyl acetate, benzene, and the like (i.e., solvents that have a high degree of solubility for the pharmacologically active agent, and are soluble in the other dispersing agent employed), along with a higher molecular weight (less volatile) dispersing agent. When added to the other dispersing agent, these volatile additives help to drive the solubility of the pharmacologically active agent into the dispersing agent. This is desirable since this step is usually time consuming. Following dissolution, the volatile component may be removed by evaporation (optionally under vacuum).

Particles of pharmacologically active agent substantially completely contained within a polymeric shell, prepared as described above, are delivered as a suspension in a biocompatible aqueous liquid. This liquid may be selected from water, saline, a solution containing appropriate buffers, a solution containing nutritional agents such as amino acids, sugars, proteins, carbohydrates, vitamins or fat, and the like.

In accordance with another embodiment of the present invention, there is provided a method for the preparation of a substantially water insoluble pharmacologically active agent for in vivo delivery, said method comprising subjecting a mixture comprising:

dispersing agent containing said pharmacologically active agent dispersed therein, and aqueous medium containing biocompatible polymer capable of being crosslinked by disulfide bonds to sonication conditions for a time sufficient to promote crosslinking of said biocompatible polymer by disulfide bonds.

A nonobvious feature of the above-described process is in the choice of dispersing agent, specifically with respect to the polarity of the dispersing agent. The formation of a shell about the particles of pharmacologically active agent involves unfolding and reorientation of the polymer at the interface between the aqueous and non-aqueous phases such that the hydrophilic regions within the polymer are exposed to the aqueous phase while the hydrophobic regions within the polymer are oriented towards the non-aqueous phase. In order to effect unfolding of the polymer, or change the conformation thereof, energy must be supplied to the polymer. The interfacial free energy (interfacial tension) between the two liquid phases (i.e., aqueous and non-aqueous) contributes to changes in polymer conformation at that interface. Thermal energy also contributes to the energy pool required for unfolding and/or change of polymer conformation.

Thermal energy input is a function of such variables as the acoustic power employed in the sonication process, the sonication time, the nature of the material being subjected to sonication, the volume of the material being subjected to sonication, and the like. The acoustic power of sonication processes can vary widely, typically falling in the range of about 1 up to 1000 watts/cm$^2$; with an acoustic power in the range of about 50 up to 200 watts/cm$^2$ being a presently preferred range. Similarly, sonication time can vary widely, typically falling in the range of a few seconds up to about 5 minutes. Preferably, sonication time will fall in the range of about 15 up to 60 seconds. Those of skill in the art recognize that the higher the acoustic power applied, the less sonication time is required, and vice versa.

The interfacial free energy is directly proportional to the polarity difference between the two liquids. Thus at a given operating temperature a minimum free energy at the interface between the two liquids is essential to form the desired polymer shell. Thus, if a homologous series of dispersing agents is taken with a gradual change in polarity, e.g., ethyl esters of alkanoic acids, then higher homologues are increasingly nonpolar, i.e., the interfacial tension between these dispersing agents and water increases as the number of carbon atoms in the ester increases. Thus it is found that, although ethyl acetate is water-immiscible (i.e., an ester of a 2 carbon acid), at room temperature (~20° C.), this dispersing agent alone will not give a significant yield of polymer shell-coated particles. In contrast, a higher ester such as ethyl octanoate (ester of an 8 carbon acid) gives polymer shell-coated particles in high yield. In fact, ethyl heptanoate (ester of a 7 carbon acid) gives a moderate yield while the lower esters (esters of 3, 4, 5, or 6 carbon acids) give poor yield. Thus, at a given temperature, one could set a condition of minimum aqueous-dispersing agent interfacial tension required for formation of high yields of polymer shell-coated particles.

Temperature is another variable that may be manipulated to affect the yield of polymer shell-coated particles. In general the surface tension of a liquid decreases with increasing temperature. The rate of change of surface tension with temperature is often different for different liquids. Thus, for example, the interfacial tension ($\Delta\gamma$) between two liquids may be $\Delta\gamma_1$ at temperature $T_1$ and $\Delta\gamma_2$ at temperature $T_2$. If $\Delta\gamma_1$ at $T_1$ is close to the minimum required to form polymeric shells of the present invention, and if $\Delta\gamma_2$ (at temp. $T_2$) is greater than $\Delta\gamma_1$, then a change of temperature from $T_1$ to $T_2$ will increase the yield of polymeric shells. This, in fact, is observed in the case of ethyl heptanoate, which gives a moderate yield at 20° C. but gives a high yield at 10° C.

Temperature also affects the vapor pressure of the liquids employed. The lower the temperature, the lower the total vapor pressure. The lower the total vapor pressure, the more efficient is the collapse of the cavitation bubble. A more efficient collapse of the sonication bubble correlates with an increased rate of superoxide ($HO_2^-$) formation. Increased rate of superoxide, formation leads to increased yields of polymeric shells at lower temperatures. As a countervailing consideration, however, the reaction rate for oxidation of sulfhydryl groups (i.e., to form disulfide linkages) by superoxide ions increases with increasing temperature. Thus for a given liquid subjected to sonication conditions, there exists a fairly narrow range of optimum operating temperatures within which a high yield of polymeric shells is obtained.

Thus a combination of two effects, i.e., the change in surface tension with temperature (which directly affects unfolding and/or conformational changes of the polymer) and the change in reaction yield (the reaction being crosslinking of the polymer via formation of disulfide linkages) with temperature dictate the overall conversion or yield of polymer shell-coated particles.

The sonication process described above may be manipulated to produce polymer shell-coated particles containing pharmacologically active agent having a range of sizes. Presently preferred particle radii fall in the range of about 0.1 up to about 5 micron. A narrow size distribution in this range is very suitable for intravenous drug delivery. The polymer shell-coated particles are then suspended in an aqueous biocompatible liquid (as described above) prior to administration by suitable means.

Variations on the general theme of dissolved pharmacologically active agent enclosed within a polymeric shell are possible. A suspension of fine particles of pharmacologically active agent in a biocompatible dispersing agent could be used (in place of a biocompatible dispersing agent containing dissolved pharmacologically active agent) to produce a polymeric shell containing dispersing agent-suspended pharmacologically active agent particles. In other words, the polymeric shell could contain a saturated solution of pharmacologically active agent in dispersing agent. Another variation is a polymeric shell containing a solid core of pharmacologically active agent produced by initially dissolving the pharmacologically active agent in a volatile organic solvent (e.g. benzene), forming the polymeric shell and evaporating the volatile solvent under vacuum, e.g., in a rotary evaporator, or freeze-drying the entire suspension. This results in a structure having a solid core of pharmacologically active agent surrounded by a polymer coat. This latter method is particularly advantageous for delivering high doses of pharmacologically active agent in a relatively small volume. In some cases, the polymer forming the shell about the core could itself be a therapeutic or diagnostic agent, e.g., in the case of insulin, which may be delivered as part of a polymeric shell formed in the sonication process described above.

Variations in the polymeric shell are also possible. For example, a small amount of PEG containing sulfhydryl groups could be included with the polymer. Upon sonication, the PEG is crosslinked into the polymer and forms a component of the polymeric shell. PEG is known for its nonadhesive character and has been attached to proteins and enzymes to increase their circulation time in vivo [Abuchowski et al., J. Biol. Chem. Vol. 252:3578 (1977)]. It has also been attached to phospholipids forming the lipidic bilayer in liposomes to reduce their uptake and prolong lifetimes in vivo [Klibanov et al., FEBS Letters Vol. 268:235 (1990)]. Thus the incorporation of PEG into the walls of crosslinked protein shells alters their blood circulation time. This property can be exploited to maintain higher blood levels of the pharmacologically active agent and prolonged pharmacologically active agent release times.

One skilled in the art will recognize that several variations are possible within the scope and spirit of this invention. The dispersing agent within the polymeric shell may be varied, a large variety of pharmacologically active agents may be utilized, and a wide range of proteins as well as other natural and synthetic polymers may be used in the formation of the walls of the polymeric shell. Applications are also fairly wide ranging. Other than biomedical applications such as the delivery of drugs, diagnostic agents (in imaging applications), artificial blood (sonochemically crosslinked hemoglobin) and parenteral nutritional agents, the polymeric shell structures of the invention may be incorporated into cosmetic applications such as skin creams or hair care products, in perfumery applications, in pressure sensitive inks, and the like.

An approach to the problem of taxol administration that has not been described in the literature is its delivery as an aqueous suspension of micron size particles, or an aqueous suspension containing either particles of taxol or taxol dissolved in a biocompatible non-aqueous liquid. This approach would facilitate the delivery of taxol at relatively high concentrations and obviate the use of emulsifiers and their associated toxic side effects.

In accordance with yet another embodiment of the present invention, the above-described mode of administration is facilitated by novel taxol-containing compositions wherein taxol is suspended in a biocompatible liquid, and wherein the resulting suspension contains particles of taxol having a cross-sectional dimension no greater than about 10 microns.

The desired particle size of less than about 10 microns can be achieved in a variety of ways, e.g., by grinding, spray drying, precipitation, sonication, and the like.

Due to the crystal size of conventionally obtained taxol which is greater than 20 microns, solid particles of taxol have not been delivered in the form of a suspension in a vehicle such as normal saline. However, the present invention discloses the delivery of a particulate suspension of taxol ground to a size less than 10 microns, preferably less than 5 microns and most preferably less than 1 micron, which allows intravenous delivery in the form of a suspension without the risk of blockage in the microcirculation of organs and tissues.

Due to the microparticular nature of the delivered drug, most of it is cleared from the circulation by organs having reticuloendothelial systems such as the spleen, liver, and lungs. This allows pharmacologically active agents in particulate form to be targeted to such sites within the body.

Biocompatible liquids contemplated for use in this embodiment are the same as those described above. In addition, parenteral nutritional agents such as Intralipid (trade name for a commercially available fat emulsion used as a parenteral nutrition agent; available from Kabi Vitrum, Inc., Clayton, N.C.), Nutralipid (trade name for a commercially available fat emulsion used as a parenteral nutrition agent; available from McGaw, Irvine, Calif.), Liposyn III (trade name for a commercially available fat emulsion used as a parenteral nutrition agent (containing 20% soybean oil, 1.2% egg phosphatides, and 2.5% glycerin); available from Abbott Laboratories, North Chicago, Ill.), and the like may be used as the carrier of the drug particles. Alternatively, if the biocompatible liquid contains a drug-solubilizing material such as soybean oil (e.g., as in the case of Intralipid), the drug may be partially or completely solubilized within the carrier liquid, aiding its delivery. An example of such a case is the delivery of taxol in Intralipid as the carrier. Presently preferred biocompatible liquids for use in this embodiment are parenteral nutrition agents, such as those described above.

In accordance with still another embodiment of the present invention, there is provided a composition for the in vivo delivery of taxol wherein taxol is dissolved in a parenteral nutrition agent.

The invention will now be described in greater detail by reference to the following non-limiting examples.

EXAMPLE 1

Preparation of Taxol Particles

Crystals of taxol (Sigma Chemical) were ground in a ball mill until particles of solid taxol were obtained having a size less than 10 microns. Size of particles were determined by suspending the particles in isotonic saline and counting with the aid of a particle counter (Elzone, Particle Data). Grinding was continued until 100% of the particles had a size less than 5 microns. The preferred particle size for intravenous delivery is less than 5 microns and most preferably less than 1 micron.

Alternatively, particles of taxol were obtained by sonicating a suspension of taxol in water until all particles were below 10 microns.

Taxol particles less than 10 microns can also be obtained by precipitating taxol from a solution of taxol in ethanol by adding water until a cloudy suspension is obtained. Optionally, the solution of taxol can be sonicated during the water addition, until a cloudy suspension is obtained. The resulting suspension is then filtered and dried to obtain pure taxol particles in the desired size range.

Fine particles of taxol were prepared by spray drying a solution of taxol in a volatile organic such as ethanol. The solution was passed through an ultrasonic nozzle that formed droplets of ethanol containing taxol. As the ethanol evaporated in the spray drier, fine particles of taxol were obtained. Particle size can be varied by changing the concentration of taxol in ethanol, adjusting the flow rate of liquid through the nozzle and power of sonication.

EXAMPLE 2

Preparation of Protein Shell Containing Oil

Three ml of a USP (United States Pharmacopeia) 5% human serum albumin solution (Alpha Therapeutic Corporation) were taken in a cylindrical vessel that could be attached to a sonicating probe (Heat Systems, Model XL2020). The albumin solution was overlayered with 6.5 ml of USP grade soybean oil (soya oil). The tip of the sonicator probe was brought to the interface between the two solutions and the assembly was maintained in a cooling bath at 20° C. The system was allowed to equilibriate and the sonicator turned on for 30 seconds. Vigorous mixing occurred and a white milky suspension was obtained. The suspension was diluted 1:5 with normal saline. A particle counter (Particle Data Systems, Elzone, Model 280 PC) was utilized to determine size distribution and concentration of oil-containing protein shells. The resulting protein shells were determined to have a maximum cross-sectional dimension of about 1.35±0.73 microns, and the total concentration determined to be ~$10^9$ shells/ml in the original suspension.

EXAMPLE 3

Parameters Affecting Polymeric Shell Formation

Several variables such as protein concentration, temperature, sonication time, concentration of pharmacologically active agent, and acoustic intensity were tested to optimize formation of polymeric shell. These parameters were determined for crosslinked bovine serum albumin shells containing toluene.

Polymeric shells made from solutions having protein concentrations of 1%, 2.5%, 5% and 10% were counted with the particle counter to determine a change in the size and number of polymeric shells produced. The size of the polymeric shells was found not to vary with protein concentration, but the number of polymeric shells per ml of "milky suspension" formed increased with the increase in concentration of the protein up to 5%. No significant change in the number of polymeric shells was found to occur above that concentration.

Initial vessel temperatures were found to be important for optimal preparation of polymeric shells. Typically, initial vessel temperatures were maintained between 0° C. and 45° C. The aqueous-oil interfacial tension of the oils used for formation of the polymeric shell was an important parameter, which also varied as a function of temperature. The concentration of pharmacologically active agent was found not to significantly effect the yield of protein shells. It is relatively unimportant if the pharmacologically active agent is incorporated in the dissolved state, or suspended in the dispersing medium.

Sonication time was an important factor determining the number of polymeric shells produced per ml. It was found that a sonication time greater than three minutes produced a decrease in the overall count of polymeric shells, indicating possible destruction of polymeric shells due to excessive sonication. Sonication times less than three minutes were found to produce adequate numbers of polymeric shells.

According to the nomograph provided by the manufacturer of the sonicator, the acoustic power rating of the sonicator employed herein is approximately 150 watts/$cm^2$. Three power settings in order of increasing power were used, and it was found that the maximum number of polymeric shells were produced at the highest power setting.

EXAMPLE 4

Preparation of Polymeric Shells Containing Dissolved Taxol

Taxol was dissolved in USP grade soybean oil at a concentration of 2 mg/ml. 3 ml of a USP 5% human serum albumin solution was taken in a cylindrical vessel that could be attached to a sonicating probe. The albumin solution was overlayered with 6.5 ml of soybean oil/taxol solution. The tip of the sonicator probe was brought to the interface between the two solutions and the assembly was maintained in equilibrium and the sonicator turned on for 30 seconds. Vigorous mixing occurred and a stable white milky suspension was obtained which contained protein-walled polymeric shells enclosing the oil/taxol solution.

In order to obtain a higher loading of drug into the crosslinked protein shell, a mutual solvent for the oil and the drug (in which the drug has a considerably higher solubility) can be mixed with the oil. Provided this solvent is relatively non-toxic (e.g., ethyl acetate), it may be injected along with the original carrier. In other cases, it may be removed by evaporation of the liquid under vacuum following preparation of the polymeric shells.

EXAMPLE 5

Stability of Polymeric Shells

Suspensions of polymeric shells at a known concentration were analyzed for stability at three different temperatures (i.e., 4° C., 25° C., and 38° C.) Stability was measured by the change in particle counts over time. Crosslinked protein (albumin) shells containing soybean oil (SBO) were prepared as described above (see Example 2), diluted in saline to a final oil concentration of 20% and stored at the above temperatures. Particle counts (Elzone) obtained for each of the samples as a function of time are summarized in Table 1.

TABLE 1

| | Protein Shells (#/ml · $10^{10}$) in saline | | |
|---|---|---|---|
| Day | 4° C. | 25° C. | 38° C. |
| 0 | 7.9 | 8.9 | 8.1 |
| 1 | 7.4 | 6.9 | 6.8 |
| 7 | 7.3 | 8.3 | 5.0 |
| 9 | 7.8 | 8.1 | 5.8 |
| 17 | 7.8 | 8.3 | 6.1 |
| 23 | 6.9 | 7.8 | 7.4 |
| 27 | 7.2 | 8.8 | 7.1 |

As demonstrated by the above data, the concentration of counted particles (i.e., polymeric shells) remains fairly constant over the duration of the experiment. The range is fairly constant and remains between about $7-9.10^{10}$/ml, indicating good polymeric shell stability under a variety of temperature conditions over almost four weeks.

EXAMPLE 6

In Vivo Biodistribution-Crosslinked Protein Shells Containing a Fluorophore

To determine the fate of crosslinked albumin shells following intravenous injection, a fluorescent dye (rubrene, obtained from Aldrich) was dissolved in toluene, and crosslinked albumin shells containing toluene/rubrene were prepared as described above by sonication. The resulting milky suspension was diluted five times in normal saline. Two ml of the diluted suspension was then injected into the tail vein of a rat over 10 minutes. One animal was sacrificed an hour after injection and another 24 hours after injection.

Frozen lung, liver, kidney, spleen, and bone marrow sections were examined under fluorescence for the presence of polymeric shells containing fluorescent dye. At one hour, most of the polymeric shells were intact and found in the lungs and liver as brightly fluorescing particles of about 1 micron diameter. At 24 hours, polymeric shells were found in the liver, lungs, spleen, and bone marrow. A general staining of the tissue was also observed, indicating that the polymeric shells had been digested, and the dye liberated from within. This result was consistent with expectations and demonstrates the potential use of invention compositions for delayed or controlled release of entrapped pharmaceutical agent such as taxol.

EXAMPLE 7

Toxicity of Polymeric Shells Containing Soybean Oil (SBO)

Polymeric shells containing soybean oil were prepared as described in Example 2. The resulting suspension was diluted in normal saline to produce two different solutions, one containing 20% SBO and the other containing 30% SBO.

Intralipid, a commercially available TPN agent, contains 20% SBO. The $LD_{50}$ for Intralipid in mice is 120 ml/kg, or about 4 ml for a 30 g mouse, when injected at 1 cc/min.

Two groups of mice (three mice in each group; each mouse weighing about 30 g) were treated with invention composition containing SBO as follows. Each mouse was injected with 4 ml of the prepared suspension of SBO-containing polymeric shells. Each member of one group received the suspension containing 20% SBO, while each member of the other group receive the suspension containing 30% SBO.

All three mice in the group receiving the suspension containing 20% SBO survived such treatment, and showed no gross toxicity in any tissues or organs when observed one week after SBO treatment. Only one of the three mice in the group receiving suspension containing 30% SBO died after injection. These results clearly demonstrate that oil contained within polymeric shells according to the present invention is not toxic at its $LD_{50}$ dose, as compared to a commercially available SBO formulation (Intralipid). This effect can be attributed to the slow release (i.e., controlled rate of becoming bioavailable) of the oil from within the polymeric shell. Such slow release prevents the attainment of a lethal dose of oil, in contrast to the high oil dosages attained with commercially available emulsions.

EXAMPLE 8

In vivo Bioavailability of Soybean Oil Released from Polymeric Shells

A test was performed to determine the slow or sustained release of polymeric shell-enclosed material following the injection of a suspension of polymeric shells into the blood stream of rats. Crosslinked protein (albumin) walled polymeric shells containing soybean oil (SBO) were prepared by sonication as described above. The resulting suspension of oil-containing polymeric shells was diluted in saline to a final suspension containing 20% oil. Five ml of this suspension was injected into the cannulated external jugular vein of rats over a 10 minute period. Blood was collected from these rats at several time points following the injection and the level of triglycerides (soybean oil is predominantly triglyceride) in the blood determined by routine analysis.

Five ml of a commercially available fat emulsion (Intralipid, an aqueous parenteral nutrition agent—containing 20% soybean oil, 1.2% egg yolk phospholipids, and 2.25% glycerin) was used as a control. The control utilizes egg phosphatide as an emulsifier to stabilize the emulsion. A comparison of serum levels of the triglycerides in the two cases would give a direct comparison of the bioavailability of the oil as a function of time. In addition to the suspension of polymeric shells containing 20% oil, five ml of a sample of oil-containing polymeric shells in saline at a final concentration of 30% oil was also injected. Two rats were used in each of the three groups. The blood levels of triglycerides in each case are tabulated in Table 2, given in units of mg/dl.

TABLE 2

| | SERUM TRIGLYCERIDES (mg/dl) | | | | | |
|---|---|---|---|---|---|---|
| GROUP | Pre | 1 hr | 4 hr | 24 hr | 48 hr | 72 hr |
| Intralipid Control (20% SBO) | 11.4 | 941.9 | 382.9 | 15.0 | 8.8 | 23.8 |
| Polymeric Shells (20% SBO) | 24.8 | 46.7 | 43.8 | 29.3 | 24.2 | 43.4 |
| Polymeric Shells (30% SBO) | 33.4 | 56.1 | 134.5 | 83.2 | 34.3 | 33.9 |

Blood levels before injection are shown in the column marked 'Pre'. Clearly, for the Intralipid control, very high triglyceride levels are seen following injection. Triglyceride levels are then seen to take about 24 hours to come down to preinjection levels. Thus the oil is seen to be immediately available for metabolism following injection.

The suspension of oil-containing polymeric shells containing the same amount of total oil as Intralipid (20%) show a dramatically different availability of detectable triglyceride in the serum. The level rises to about twice its normal value and is maintained at this level for many hours, indicating a slow or sustained release of triglyceride into the blood at levels fairly close to normal. The group receiving oil-containing polymeric shells having 30% oil shows a higher level of triglycerides (concomitant with the higher administered dose) that falls to normal within 48 hours. Once again, the blood levels of triglyceride do not rise astronomically in this group, compared to the control group receiving Intralipid. This again, indicates the slow and sustained availability of the oil from invention composition, which has the advantages of avoiding dangerously high blood levels of material contained within the polymeric shells and availability over an extended period at acceptable levels. Clearly, drugs delivered within polymeric shells of the present invention would achieve these same advantages.

Such a system of soybean oil-containing polymeric shells could be suspended in an aqueous solution of amino acids, essential electrolytes, vitamins, and sugars to form a total parenteral nutrition (TPN) agent. Such a TPN cannot be formulated from currently available fat emulsions (e.g., Intralipid) due to the instability of the emulsion in the presence of electrolytes.

EXAMPLE 9

Preparation of Crosslinked Protein-walled Polymeric Shells Containing a Solid Core of Pharmaceutically Active Agent Another method of delivering a poorly water-soluble drug such as taxol within a polymeric shell is to prepare a shell of polymeric material around a solid drug core. Such a 'protein coated' drug particle may be obtained as follows. The procedure described in Example 4 is repeated using an organic solvent to dissolve taxol at a relatively high concentration. Solvents generally used are organics such as benzene, toluene, hexane, ethyl ether, and the like. Polymeric shells are produced as described in Example 4. Five ml of the milky suspension of polymeric shells containing dissolved taxol are diluted to 10 ml in normal saline. This suspension is placed in a rotary evaporator at room temperature and the volatile organic removed by vacuum. After about 2 hours in the rotary evaporator, these polymeric shells are examined under a microscope to reveal opaque cores, indicating removal of substantially all organic solvent, and the presence of solid taxol within a shell of protein.

Alternatively, the polymeric shells with cores of organic solvent-containing dissolved drug are freeze-dried to obtain a dry crumbly powder that can be resuspended in saline (or other suitable liquid) at the time of use. In case of other drugs that may not be in the solid phase at room temperature, a liquid core polymeric shell is obtained. This method allows for the preparation of a crosslinked protein-walled shell containing undiluted drug within it. Particle size analysis shows these polymeric shells to be smaller than those containing oil. Although the presently preferred protein for use in the formation of the polymeric shell is albumin, other proteins such as α-2-macroglobulin, a known opsonin, could be used to enhance uptake of the polymeric shells by macrophage-like cells. Alternatively, a PEG-sulfhydryl (described below) could be added during formation of the polymeric shell to produce a polymeric shell with increased circulation time in vivo.

EXAMPLE 10

In vivo Circulation and Release Kinetics of Polymeric Shells

Solid core polymeric shells containing taxol were prepared as described above (see, for example, Example 4) and suspended in normal saline. The concentration of taxol in the suspension was measured by HPLC as follows. First, the taxol within the polymeric shell was liberated by the addition of 0.1M mercaptoethanol (resulting in exchange of protein disulfide crosslinkages, and breakdown of the crosslinking of the polymeric shell), then the liberated taxol was extracted from the suspension with acetonitrile. The resulting mixture was centrifuged and the supernatant freeze-dried. The lyophilate was dissolved in methanol and injected onto an HPLC to determine the concentration of taxol in the suspension. The taxol concentration was found to be about 1.6 mg/ml.

Rats were injected with 2 ml of this suspension through a jugular catheter. The animal was sacrificed at two hours, and the amount of taxol present in the liver determined by HPLC. This required homogenization of the liver, followed by extraction with acetonitrile and lyophilization of the supernatant following centrifugation. The lyophilate was dissolved in methanol and injected onto an HPLC. Approximately 15% of the administered dose of taxol was recovered from the liver at two hours, indicating a significant dosage to the liver. This result is consistent with the known function of the reticuloendothelial system of the liver in clearing small particles from the blood.

EXAMPLE 11

Preparation of Crosslinked PEG-walled Polymeric Shells

As an alternative to the use of thiol (sulfhydryl) containing proteins in the formation of, or as an additive to polymeric shells of the invention, a thiol-containing PEG was prepared. PEG is known to be nontoxic, noninflammatory, nonadhesive to cells, and in general biologically inert. It has been bound to proteins to reduce their antigenicity and to liposome forming lipids to increase their circulation time in vivo. Thus incorporation of PEG into an essentially protein shell would be expected to increase circulation time as well as stability of the polymeric shell. By varying the concentration of PEG-thiol added to the 5% albumin solution, it was possible to obtain polymeric shells with varying stabilities in vivo. PEG-thiol was prepared by techniques available in the literature (such as the technique of Harris and Herati, as described in Polymer Preprints Vol. 32:154–155 (1991)).

PEG-thiol of molecular weight 2000 g/mol was dissolved at a concentration of 1% (0.1 g added to 10 ml) in a 5% albumin solution. This protein/PEG solution was overlayered with oil as described in Example 2 and sonicated to produce oil-containing polymeric shells with walls comprising crosslinked protein and PEG. These Polymeric shells were tested for stability as described in Example 5.

Other synthetic water-soluble polymers that may be modified with thiol groups and utilized in lieu of PEG include, for example, polyvinyl alcohol, polyhydroxyethyl methacrylate, polyacrylic acid, polyethyloxazoline, polyacrylamide, polyvinyl pyrrolidinone, polysaccharides (such as chitosan, alginates, hyaluronic acid, dextrans, starch, pectin, etc), and the like.

EXAMPLE 12

Targeting of Immunosuppressive Agent to Transplanted Organs using Intravenous Delivery of Polymeric Shells Containing Such Agents Immunosuppressive agents are extensively used following organ transplantation for the prevention of rejection episodes. In particular, cyclosporine, a potent immunosuppressive agent, prolongs the survival of allogeneic transplants involving skin, heart, kidney, pancreas, bone marrow, small intestine, and lung in animals. Cyclosporine has been demonstrated to suppress some humoral immunity and to a greater extent, cell mediated reactions such as allograft rejection, delayed hypersensitivity, experimental allergic encephalomyelitis, Freund's adjuvant arthritis, and graft versus host disease in many animal species for a variety of organs. Successful kidney, liver and heart allogeneic transplants have been performed in humans using cyclosporine.

Cyclosporine is currently delivered in oral form either as capsules containing a solution of cyclosporine in alcohol, and oils such as corn oil, polyoxyethylated glycerides and the like, or as a solution in olive oil, polyoxyethylated glycerides, etc. It is also administered by intravenous injection, in which case it is dissolved in a solution of ethanol (approximately 30%) and Cremaphor (polyoxyethylated castor oil) which must be diluted 1:20 to 1:100 in normal saline or 5% dextrose prior to injection. Compared to an intravenous (i.v.) infusion, the absolute bioavailibility of the oral solution is approximately 30% (Sandoz Pharmaceutical Corporation, Publication SDI-Z10 (A4), 1990). In general, the i.v. delivery of cyclosporine suffers from similar problems as the currently practiced i.v. delivery of taxol, i.e., anaphylactic and allergic reactions believed to be due to the Cremaphor, the delivery vehicle employed for the i.v. formulation.

In order to avoid problems associated with the Cremaphor, cyclosporine contained within polymeric shells as described above may be delivered by i.v. injection. It may be dissolved in a biocompatible oil or a number of other solvents following which it may be dispersed into polymeric shells by sonication as described above. In addition, an important advantage to delivering cyclosporine (or other immunosuppressive agent) in polymeric shells has the advantage of local targeting due to uptake of the injected material by the RES system in the liver. This may, to some extent, avoid systemic toxicity and reduce effective dosages due to local targeting. The effectiveness of delivery and targeting to the liver of taxol contained within polymeric shells following intravenous injection is demonstrated in Example 9. A similar result would be expected for the delivery of cyclosporine (or other putative immunosuppressive agent) in accordance with the present invention.

While the invention has been described in detail with reference to certain preferred embodiments thereof, it will be understood that modifications and variations are within the spirit and scope of that which is described and claimed.

That which is claimed is:

1. A method for the preparation of a substantially water insoluble pharmacologically active agent for in vivo delivery, said method comprising subjecting a mixture comprising:

a dispersing agent containing said pharmacologically active agent dispersed therein, and aqueous medium containing a biocompatible polymer capable of being crosslinked by disulfide bonds to sonication conditions for a time sufficient to promote crosslinking of said biocompatible polymer by disulfide bonds to produce a polymeric shell containing the pharmacologically active agent therein.

2. A method for the preparation of substantially water insoluble pharmaceutical agents for in vivo delivery, said method comprising subjecting taxol and suitable medium to sonication conditions for a time sufficient to produce particles having a maximum cross-sectional dimension of no greater than about 10 microns.

3. The method according to claim 1 wherein said dispersing agent is selected from soybean oil, coconut oil, olive oil, safflower oil, cotton seed oil, aliphatic, cycloaliphatic or aromatic hydrocarbons having 4–30 carbon atoms, aliphatic or aromatic alcohols having 2–30 carbon atoms, aliphatic or aromatic esters having 2–30 carbon atoms, alkyl, aryl, or cyclic ethers having 2–30 carbon atoms, alkyl or aryl halides having 1–30 carbon atoms, optionally having more than one halogen substituent, ketones having 3–30 carbon atoms, polyalkylene glycol, or combinations of any two or more thereof.

4. The method according to claim 3 wherein said dispersing agent comprises a volatile dispersing agent.

5. The method according to claim 4 wherein the volatile dispersing agent is selected from benzene, toluene, hexane, ethyl ether, dichloromethane, or ethyl acetate.

6. The method according to claim 1 wherein said substantially water insoluble pharmacologically active agent is selected from a pharmaceutically active agent, a diagnostic agent, or an agent of nutritional value.

7. The method according to claim 6 wherein said pharmaceutically active agent is selected from taxol, taxotere, campothecin, aspirin, ibuprofen, piroxicam, cimetidine, substantially water insoluble steroids, phenesterine, duanorubicin, doxorubicin, mitotane, visadine, halonitrosoureas, anthrocylines, ellipticine, diazepam, methoxyfluorane, isofluorane, enfluorane, halothane, benzocaine, dantrolene, or barbiturates.

8. The method according to claim 6 where said pharmaceutically active agent is a substantially water insoluble immunosuppressive agent selected from cyclosporines, azathioprine, 17-ally-1,14-dihydroxy-12-[2-(4-hydroxy-3-methoxycyclohexyl)-1-methylvinyl]-23,25-dimethoxy-13,19,21,27-tetramethyl-11,28 -dioxa-4-azatricyclo [22.3.1.0$^{4,9}$]octacos-18-ene-2,3,10,16-tetraone, or prednisone.

9. The method according to claim 6 wherein said diagnostic agent is selected from ultrasound contrast agents radiocontrast agents, or magnetic contrast agents.

10. The method according to claim 9 wherein said radiocontrast agent is selected from iodo-octanes, halocarbons, or renografin.

11. The method according to claim 9 wherein said magnetic contrast agent is a lipid soluble paramagnetic compound.

12. The method according to claim 6 wherein said agent of nutritional value is selected from amino acids, sugars, proteins, carbohydrates, fat-soluble vitamins, or fat, or combinations of any two or more thereof.

13. The method according to claim 12 wherein said pharmacologically active agent within said shell is dissolved in a biocompatible dispersing agent.

14. The method according to claim 1 wherein said pharmacologically active agent within said shell is suspended in a biocompatible dispersing agent.

15. The method according to claim 1 further comprising suspending the polymeric shells in a biocompatible aqueous liquid.

16. The method according to claim 15 wherein said biocompatible aqueous liquid is selected from water, saline, a solution containing appropriate buffers, or a solution containing nutritional agents.

17. The method according to claim 1 wherein said biocompatible polymer is a naturally occurring polymer, a synthetic polymer, or a combination thereof, wherein said polymer, prior to crosslinking, has covalently attached thereto sulfhydryl groups or disulfide linkages.

18. The method according to claim 17 wherein said naturally occurring polymers are selected from proteins, lipids, polynucleic acids or polysaccharides.

19. The method according to claim 18 wherein said protein is selected from albumin, insulin, hemoglobin, lysozyme, immunoglobulins, alpha-2-macroglobulin, fibronectin, vitronectin, or fibrinogen.

20. The method according to claim 19 wherein said protein is albumin.

21. The method according to claim 18 wherein said polysaccharide is selected from starch, cellulose, dextrans, alginates, chitosan, pectin, or hyaluronic acid.

22. The method according to claim 17 wherein said synthetic polymers are selected from synthetic polyamino acids containing cysteine residues and/or disulfide groups, polyvinyl alcohol modified to contain free sulfhydryl groups and/or disulfide groups, polyhydroxyethyl methacrylate modified to contain free sulfhydryl groups and/or disulfide groups, polyacrylic acid modified to contain free sulfhydryl groups and/or disulfide groups, polyethyloxazoline modified to contain free sulfhydryl groups and/or disulfide groups, polyacrylamide modified to contain free sulfhydryl groups and/or disulfide groups, polyvinyl pyrrolidone modified to contain free sulfhydryl groups and/or disulfide groups, polyalkylene glycols modified to contain free sulfhydryl groups and/or disulfide groups, as well as mixtures of any two or more thereof.

23. The method according to claim 1 wherein the mixture is subjected to sonication conditions comprising acoustic power in the range of 1 up to 1000 watts/cm$^2$.

24. The method according to claim 1 wherein the mixture is subjected to sonication conditions comprising acoustic power in the range of 50 up to 500 watts/cm$^2$.

25. The method according to claim 1 wherein the mixture is subjected to sonication for less than 5 minutes.

26. The method according to claim 1 wherein the mixture is subjected to sonication for a time ranging from 15 to 60 seconds.

27. The method according to claim 1 further comprising removing the dispersing agent from the mixture.

28. The method according to claim 1 wherein the largest cross-sectional dimension of said shell is no greater than about 10 microns.

* * * * *